United States Patent
Noguchi et al.

(10) Patent No.: US 10,591,431 B2
(45) Date of Patent: Mar. 17, 2020

(54) SENSOR ELEMENT

(71) Applicant: DENSO CORPORATION, Kariya, Aichi-pref. (JP)

(72) Inventors: Makoto Noguchi, Kariya (JP); Satoshi Suzuki, Kariya (JP)

(73) Assignee: DENSO CORPORATION, Kariya (JP)

( * ) Notice: Subject to any disclaimer, the term of this patent is extended or adjusted under 35 U.S.C. 154(b) by 85 days.

(21) Appl. No.: 16/062,897

(22) PCT Filed: Dec. 16, 2016

(86) PCT No.: PCT/JP2016/087597
§ 371 (c)(1),
(2) Date: Jun. 15, 2018

(87) PCT Pub. No.: WO2017/104818
PCT Pub. Date: Jun. 22, 2017

(65) Prior Publication Data
US 2019/0003997 A1 Jan. 3, 2019

(30) Foreign Application Priority Data
Dec. 17, 2015 (JP) ................. 2015-246409

(51) Int. Cl.
*G01N 27/12* (2006.01)
*G01M 15/10* (2006.01)
*F01N 11/00* (2006.01)

(52) U.S. Cl.
CPC .......... *G01N 27/12* (2013.01); *G01M 15/102* (2013.01); *G01N 27/125* (2013.01); *F01N 11/007* (2013.01)

(58) Field of Classification Search
CPC ...... G01N 1/22; G01N 1/2247; G01N 1/2252; G01N 27/12; G01N 27/125; G01N 27/127; G01N 27/403; G01N 27/407; G01N 27/4071; G01N 27/4075; G01N 27/4162; G01M 15/10; G01M 15/102; F01N 11/007
(Continued)

(56) References Cited

U.S. PATENT DOCUMENTS

| 2007/0245803 A1* | 10/2007 | Tan ..................... G01N 27/4077 73/31.05 |
| 2012/0061231 A1* | 3/2012 | Kobayashi ......... G01N 27/4073 204/157.42 |

(Continued)

FOREIGN PATENT DOCUMENTS

| DE | 10 2008 041 707 A1 | 3/2010 |
| JP | 2012-78130 | 4/2012 |
| JP | 2016-3932 | 1/2016 |

*Primary Examiner* — Benjamin R Schmitt
(74) *Attorney, Agent, or Firm* — Nixon & Vanderhy P.C.

(57) ABSTRACT

An electrode for a sensor element 1 that detects a specific substance in a gas to be measured, wherein the electrode is embedded in an insulating substrate having a detection face to which the specific substance adheres, the electrode being embedded in such a manner that a part of the electrode is exposed at the detection face, the electrode comprises an alloy of Pt and at least one metal selected from the group consisting of Rh, Ru, Ir, Os, and Pd, and granular voids dispersed among the alloy, and the content of the metal in the alloy is 40 mass % or less, and the number of the granular voids per unit volume of the electrode for a sensor element is $3/100\ \mu m^3$ to $50/100\ \mu m^3$.

5 Claims, 12 Drawing Sheets

(58) Field of Classification Search
USPC .................................. 73/23.2, 28.01, 31.05
See application file for complete search history.

(56) References Cited

U.S. PATENT DOCUMENTS

2015/0241384 A1    8/2015   Okamoto et al.
2015/0353742 A1   12/2015   Okamoto et al.

* cited by examiner

FIG.7
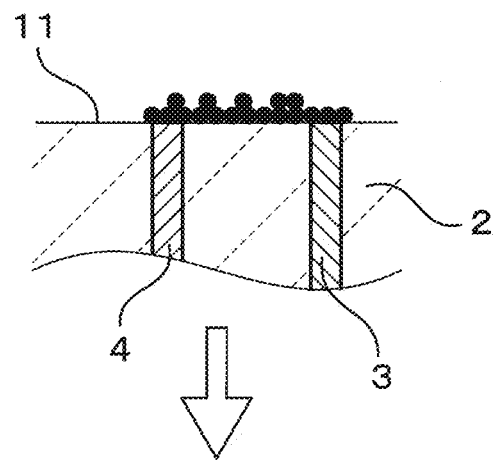
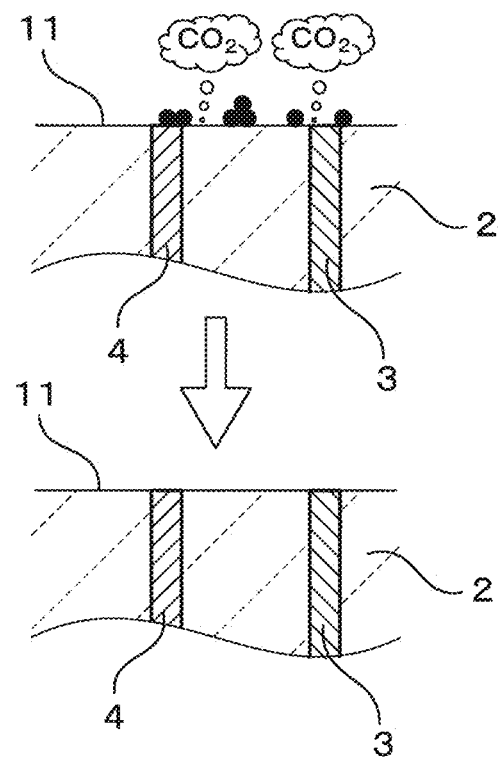

FIG.16
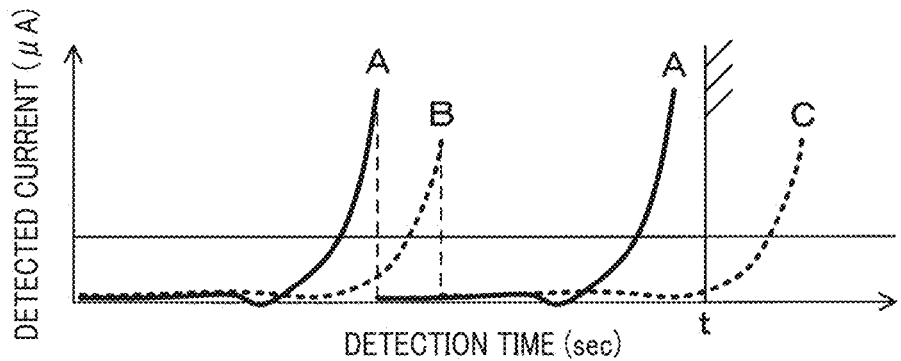
FIG.17
<SEM IMAGE OF ELEMENT CROSS SECTION (AFTER TAKING COUNTERMEASURE)>
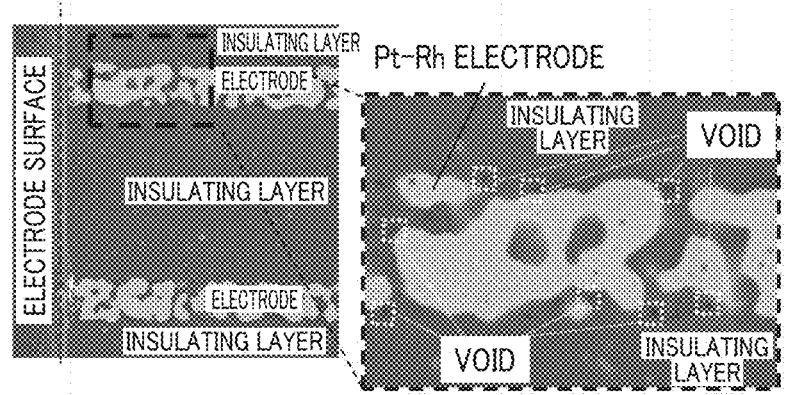
<SEM IMAGE OF ELEMENT CROSS SECTION (BEFORE TAKING COUNTERMEASURE)>
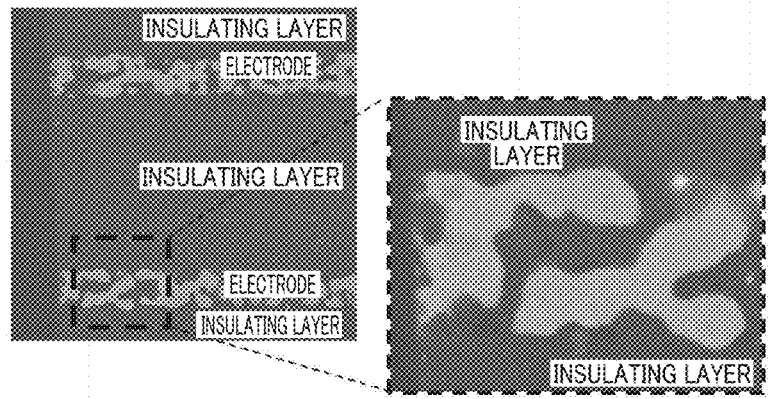

<ELECTRODE RESISTANCE MEASUREMENT RESULTS>

SENSOR ELEMENT

This application is the U.S. national phase of International Application No. PCT/JP2016/087597 filed Dec. 16, 2016, which designated the U.S. and claims priority to JP Patent Application No. 2015-246409 filed Dec. 17, 2015, the entire contents of each of which are hereby incorporated by reference.

TECHNICAL FIELD

The present disclosure relates to an electrode for a sensor element used for a particulate matter detection sensor or the like, and a sensor element using the same.

BACKGROUND ART

A particulate matter detection sensor of an electric resistance type is used to detect the amount of particulate matter (PM) in the exhaust gas discharged from an internal combustion engine. The particulate matter detection sensor has an insulating substrate and detection electrodes at least a part of which is embedded in the insulating substrate. The sensor includes a sensor element with a detection face, corresponding to an end face or a side face of the insulating substrate, at which the detection electrodes are exposed.

Over the detection face of such a sensor element, detection electrodes of different polarities are alternately disposed with an insulating layer interposed therebetween. An electrostatic field is formed by applying a voltage between these electrodes. As a result, the charged particulate matter is attracted to the electrostatic field and trapped on the detection face, thereby causing the electrodes to conduct. Thus, it is possible to detect the amount of the particulate matter contained in the exhaust gas based on the change in the resistance between the electrodes.

Typically, Pt electrodes are used as the detection electrodes. A sensor electrode of Pt or a Pt alloy for various sensors is disclosed in, for example, PTL 1. Further, PTL 2 discloses, as a detection electrode for a particulate matter detection sensor, an electrode made of Pt and a glass material having a softening temperature of 1000° C. or higher.

CITATION LIST

Patent Literature

[PTL 1] JP 2014-66547 A
[PTL 2] DE 102008041707 A

SUMMARY OF THE INVENTION

Technical Problem

The conventional Pt electrode described in PTL 1 and the like includes a ceramic particle phase as an aggregate, and thus is porous. In the Pt electrode, volatilization due to oxidation of Pt tends to occur under high temperature conditions (for example, 850° C. or higher). Therefore, when the Pt electrode is applied to a particulate matter detection sensor, there is a risk that Pt is oxidized to $PtO_2$, which has a low vapor pressure, and evaporates from the detection face and is lost. As a result, the detection electrodes gradually diminish and disappear from the detection face toward the inside of the insulating substrate, and when the detection electrodes become no longer exposed at the detection face, the distances between the electrodes become longer, resulting in deterioration in the detection accuracy.

On the other hand, in PTL 2, by adding a glass material, holes and gaps are filled during heat treatment to suppress volatilization of Pt. However, the addition of a glass material leads to an increase in the resistance as an electrode. As can be seen, at present, it is difficult to realize both the desired electrode resistance and suppressed loss of material of the detection electrodes due to volatilization/loss of Pt.

The present disclosure has been made in view of the above background, and an object of the present disclosure is to provide an electrode for a sensor element that suppresses both volatilization of Pt at the detection face and an increase in the electrode resistance to improve detection accuracy, and a sensor element which employs such electrodes.

Solution to Problem

An aspect of the present disclosure resides in an electrode for a sensor element (1) that detects a specific substance in a gas to be measured, wherein
the electrode is embedded in an insulating substrate (2) having a detection face (11) to which the specific substance adheres, the electrode being embedded in such a manner that a part of the electrode is exposed at the detection face,
the electrode includes an alloy (7) of Pt and at least one metal selected from the group consisting of Rh, Ru, Ir, Os, and Pd, and granular voids (5) dispersed among the alloy, and
the content of the metal in the alloy is 40 mass % or less, and the number of the granular voids per unit volume of the electrode for a sensor element is $3/100\ \mu m^3$ to $50/100\ \mu m^3$.

Another aspect of the present disclosure resides in a sensor element (1) that detects a specific substance in a gas to be measured, including:
an insulating substrate (2) having a detection face (11) to which the specific substance adheres; and
a pair of detection electrodes (3, 4) with different polarities, a part of each detection electrode being exposed at the detection face and facing the exposed part of the other detection electrode, and the remaining part each detection electrode being embedded in the insulating substrate, wherein
each detection electrode includes an alloy (7) of Pt and at least one metal selected from the group consisting of Rh, Ru, Ir, Os, and Pd, and granular voids (5) dispersed among the alloy, and
the content of the metal in the alloy is 40 mass % or less, and the number of the granular voids per unit volume of the detection electrodes is $3/100\ \mu m^3$ to $50/100\ \mu m^3$.

The reference signs in parentheses are given for reference, and the present disclosure is not limited by them.

Advantageous Effects of the Invention

Since an alloy of Pt and the above-described metal is used as a main component, the electrode for a sensor element provides the advantageous effect of suppressing Pt evaporating and disappearing from the detection face in a high temperature range. However, merely making the main component of the electrode an alloy is not enough, and it was found that in the high temperature range (for example, in the range of 700° C. to 800° C.), segregation of the metal inside occurs on the detection face to form a resistance layer, which results in an increase in the electrode resistance. In the above-described high temperature range, the above-described metal is also oxidized at the outermost layer. On the other hand, in the above-described electrode for a sensor element, the segregation of the metal can also be suppressed by the granular voids dispersed among the alloy. That is, granular voids are provided in the electrode for a sensor element in the range of 3/100 $\mu m^3$ to 50/100 $\mu m^3$ so that oxidation of the metal in contact with the granular voids occurs. As a result, diffusion of the metal to the electrode surface, and further, segregation of the oxide to the detection face are suppressed. In addition, it is possible to reduce the increase ratio of the electrode resistance.

The electrode for a sensor element can achieve both the suppression of volatilization and disappearance of Pt, and the suppression of increase in the electrode resistance. Therefore, according to the sensor element, the change in the electrode interval at the detection face is suppressed, whereby a low electrode resistance is maintained, and the detection accuracy is improved. The sensor element uses such electrodes for a sensor element as the pair of detection electrodes.

BRIEF DESCRIPTION OF THE DRAWINGS

FIG. 7 is a schematic view showing the PM removal process after PM detection of the sensor element according to the first embodiment.

FIG. 16 is a diagram showing the relationship of the detection current and detection time of the sensor element before and after the durability test according to Experimental Example 2, in comparison with a conventional sensor element.

FIG. 17 shows cross-sectional views and enlarged cross-sectional views of sensor elements in the vicinity of their detection faces observed with a scanning electron microscope according to a conventional element and Experimental Example 5, where Rh is chosen for the alloy among the metals shown with regard to Experimental Example 5 as a representative example.

DESCRIPTION OF THE EMBODIMENTS

First Embodiment

Next, embodiments of an electrode for a sensor element and a sensor element using the same will be described with reference to the drawings. As shown in FIGS. 1 to 5, this embodiment is an example of application to a particulate matter detection sensor including a laminated type sensor element 1. The particulate matter detection sensor is installed, for example, in the exhaust passage of an internal combustion engine to constitute a part of an exhaust post-treatment device. The sensor element 1 can detect particulate matter (hereinafter referred to as PM) as a specific substance contained in the gas to be measured. The gas to be measured is, for example, a combustion exhaust gas discharged from an internal combustion engine containing micro PM including conductive soot and the like.

Figure 1:
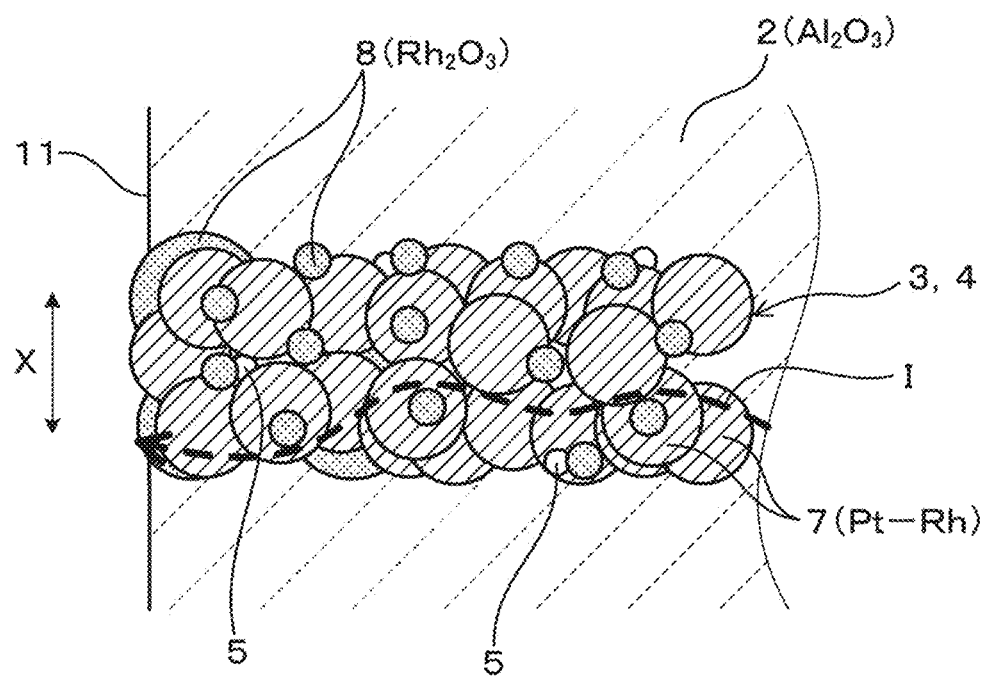
FIG. 1 is a schematic cross-sectional view of a configuration of a detection electrode of a sensor element according to a first embodiment.
Figure 2:
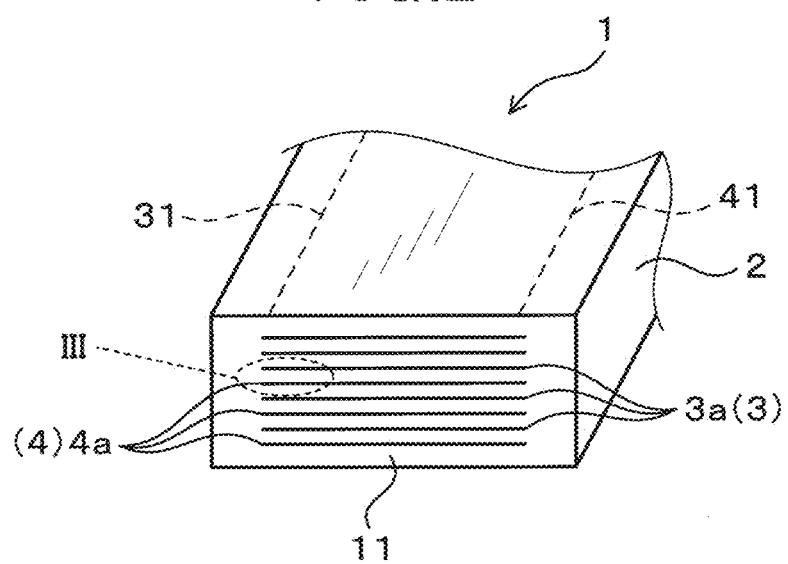
FIG. 2 is an enlarged perspective view of a part of the sensor element according to the first embodiment.
Figure 3:
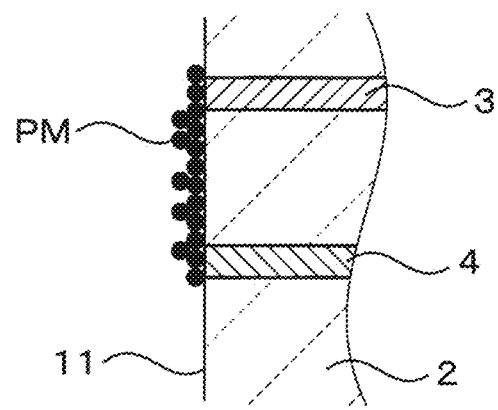
FIG. 3 is an enlarged cross-sectional view of a region III of FIG. 2 which is a part of the sensor element according to the first embodiment.

As shown in FIGS. 1 to 3, one end face of an insulating substrate 2 of the sensor element 1 serves as a detection face 11. On the detection surface 11, parts of pairing detection electrodes 3, 4 which are sensor element electrodes, are exposed to form linear electrodes. The remaining parts of the detection electrodes 3, 4 are embedded in the insulating substrate 2. As shown in FIG. 2, the detection electrode 3 and the detection electrode 4 having polarities different from each other are each composed of a plurality of electrodes 3a, 4a. The electrodes 3a, 4a are alternately arranged in the insulating substrate 2 to constitute opposing electrode pairs. The plurality of electrodes 3a, 4a constituting the detection electrodes 3, 4 is connected to lead electrodes 31, 41 inside the insulating substrate 2. The lead electrodes 31, 41 extend inside the insulating substrate 2 from the detection face 11 toward the end face on the side opposite to the detection face 11. The electrodes 3a of the detection electrode 3 and the electrodes 4a of the detection electrode 4 constituting each electrode pair have the same shape at the detection face 11 and are arranged in parallel at a predetermined interval. The spacing and the number of electrode pairs can be selected as appropriate.

Figure 4:
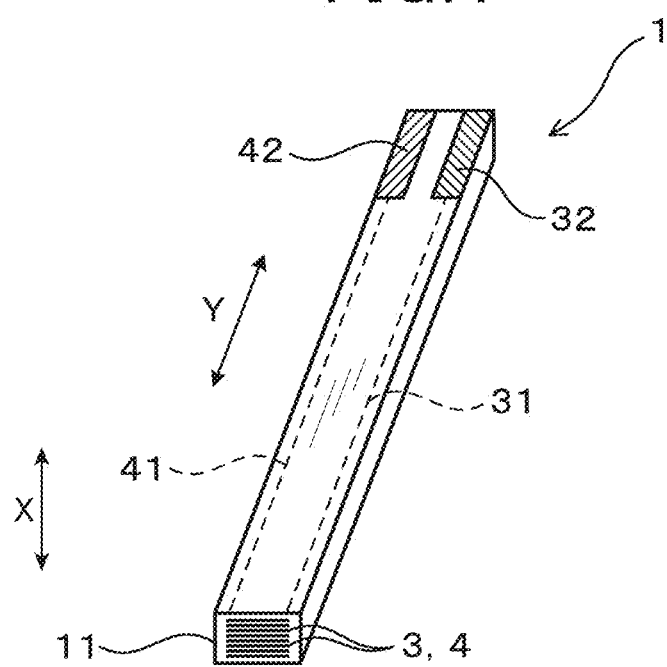
FIG. 4 is an overall perspective view of the sensor element according to the first embodiment.

As shown in FIG. 3, the exposed surfaces of the detection electrodes 3, 4 are flush with one end face of the insulating substrate 2 serving as the detection face 11. The surface of the insulating substrate 2 between the detection electrodes 3 and 4 becomes a PM collection surface. PM adheres to the detection face 11 of the sensor element 1 and accumulates on the exposed surfaces of the detection electrodes 3 and 4 and the surface of the insulating substrate 2. When the adjacent detection electrodes 3 and 4 constituting an electrode pair are electrically connected via PM, the resistance between the electrodes changes in accordance with the amount of accumulated PM. At this time, as indicated by the arrow of FIG. 1, current flows through the detection electrodes 3, 4, and the PM accumulation amount can be detected from the value of the detected current I. As shown in FIG. 4, the flow direction of the current is the longitudinal direction Y of the sensor element 1 orthogonal to the lamination direction X of the detection electrodes 3 and 4, and the direction that connects the end face on the side of the detection face 11 of the detection electrodes 3 and 4 and the end face on the other side.

The material of the insulating substrate 2 may be a ceramic material with good electrical insulation and heat resistance or a known ceramic material. Examples of the ceramic material include insulating materials such as alumina, magnesia, titania, and mullite. Examples of the known ceramic material include dielectric materials obtained by mixing alumina or zirconia with a high dielectric constant material such as barium titanate. The material of the detection electrodes 3 and 4 may be a conductive material whose main component is an alloy of Pt and at least one metal selected from the group consisting of Rh, Ru, Ir, Os, and Pd. The conductive material forming the detection electrodes 3, 4 may include the above-mentioned known ceramic material as an aggregate.

Preferably, as shown in FIG. 1, for example, the insulating substrate 2 may be made of alumina (that is, $Al_2O_3$) and the detection electrodes 3 and 4 may be made of an alloy of Pt and Rh (hereinafter referred to as Pt—Rh alloy). Inside the detection electrodes 3, 4, micro granular voids 5 are provided in a dispersed manner between alloy particles 7 of the Pt—Rh alloy or the like. In this embodiment, the granular voids 5 function as an oxygen donor part for donating oxygen to a metal such as Rh contained in the alloy particle 7 to form a metal oxide 8 such as $Rh_2O_3$. In order to obtain this function, the number of the granular voids 5 per unit volume is preferably $3/100$ $\mu m^3$ to $50/100$ $\mu m^3$. Preferably, the number of the granular voids 5 is in this range entirely along the current flow direction (that is, the direction orthogonal to the lamination direction X).

The granular voids 5 are dispersed in the detection electrodes 3, 4, embedded in the insulating substrate 2, at a predetermined ratio and throughout them. As a result, a metal oxide 8 such as $Rh_2O_3$ is formed in a dispersed manner across the detection electrodes 3, 4. Thus, it is possible to prevent metal such as Rh diffusing to the detection face 11 and causing segregation of the metal oxide 8 at the surface. In order to obtain this advantageous effect, it is preferable to control the number of the granular voids 5 per unit volume to be included in the above range, and the conductive path provided by the alloy particles 7 of the Pt—Rh alloy or the like is maintained. If the number of the granular voids 5 is less than $3/100$ $\mu m^3$, the segregation of the metal oxide 8 at the surface of the detection face 11 cannot be eliminated. If the number of the granular voids 5 is greater than $50/100$ $\mu m^3$, there will be too much metal oxide 8, and formation of the conductive path through which the detection current I flows is prevented.

The content of the metal such as Rh in the Pt alloy is desirably such that the content of the metal such as Rh is 40 mass % or less, preferably 0.5 mass % to 40 mass %, and more preferably 2 mass % to 30 mass % based on the total amount of Pt and the metal such as Rh. In addition, the size of the granular voids 5 formed inside the detection electrodes 3, 4 is normally sufficiently smaller than the average particle diameter of the alloy particles 7. For example, the particle diameter of the granular voids 5 is desirably 2.5 μm or less, preferably 1.5 μm or less. If the particle diameter of the granular voids 5 is larger than 2.5 μm, formation of the conductive path by the alloy particles 7 may be prevented.

Preferably, the granular voids 5 are dispersed such that, when the detection electrodes 3, 4 are divided into a central part and two end parts in the lamination direction X of the detection electrodes 3, 4 (that is, the direction orthogonal to the current flow direction), more granular voids 5 are present in the end parts. That is, the degree of void dispersion, which represents the unevenness of the granular voids 5 inside the detection electrodes 3, 4, is desirably greater than 0.5. The degree of void dispersion is the ratio of the number of the granular voids 5 present in the two end parts to the whole when the detection electrodes 3, 4 are equally divided into the central part and two end parts. For example, it can be calculated as the number of voids in the two end parts of the detection electrodes 3, 4/the total number of voids, in an electrode cross section in the current flow direction (that is, the direction orthogonal to the lamination direction X). When the degree of void dispersion is greater than 0.5 and more granular voids 5 are arranged in the two end parts of the detection electrodes 3 and 4, the current flow to the central part is facilitated, thereby suppressing an increase in the electrode resistance. Preferably, the degree of void dispersion is within the range of 0.55 to 0.95.

As shown in FIG. 4, the insulating substrate 2 has a cuboid shape as a whole, and one end face on one end thereof in the longitudinal direction Y will be referred to as a first face (that is, the closer end face of the insulating substrate 2 shown in FIG. 4). The end face of the insulating substrate 2 shown in FIG. 4 that is opposing the first face will be referred to as a second face. The first face is provided with the detection face 11 at which the detection electrodes 3, 4 are exposed. On the second surface, terminal electrodes 32, 42 are provided which are connected to a measurement unit (not shown). The terminal electrodes 32 and 42 are connected to the detection electrodes 3 and 4 via the lead electrodes 31 and 41, respectively, inside the insulating substrate 2.

Figure 5:
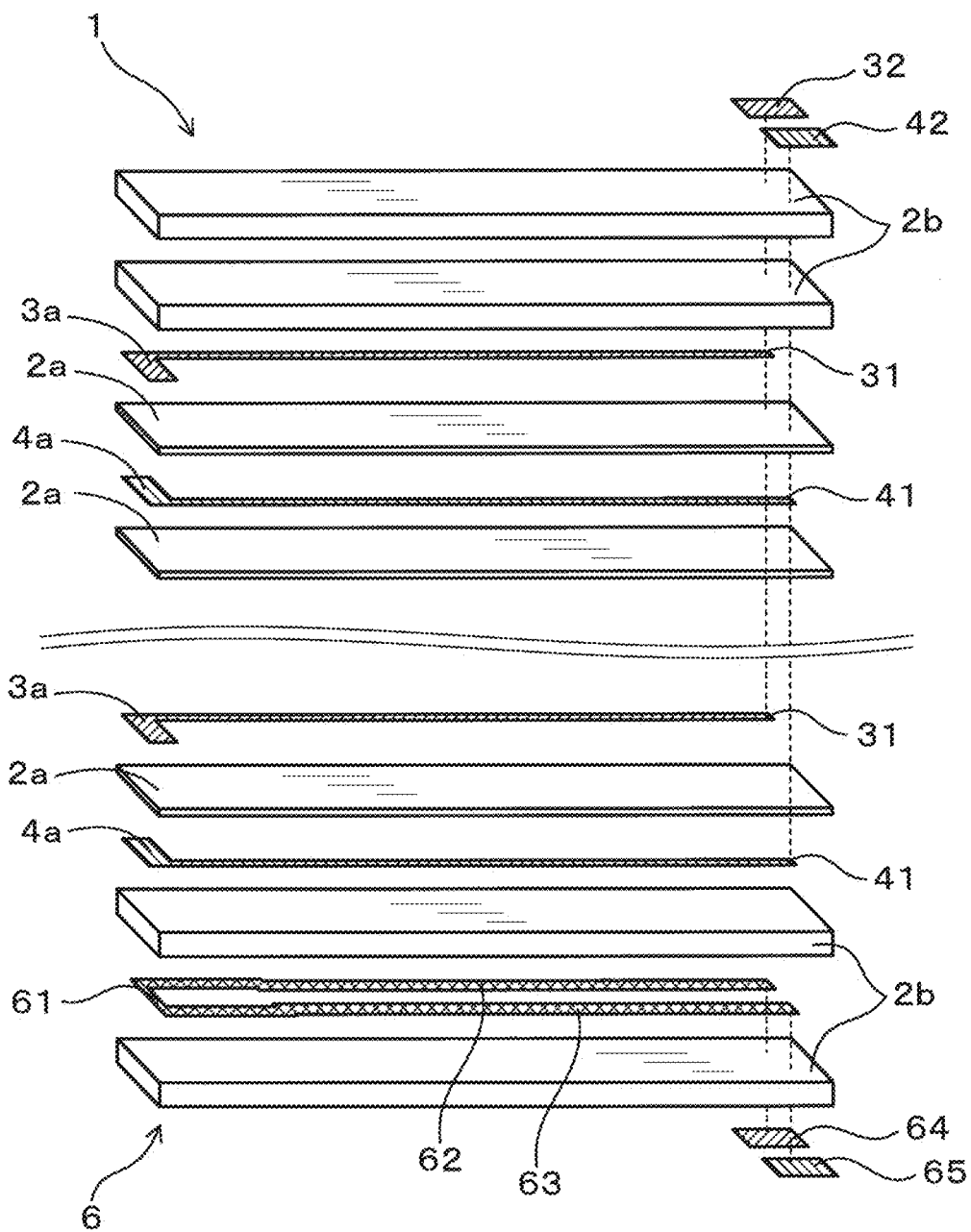
FIG. 5 is an exploded view of an overall configuration of the sensor element according to the first embodiment.

As shown in FIG. 5, the insulating substrate 2 is formed by laminating ceramic green sheets 2a, 2b made of the above-mentioned ceramic material such as alumina. The electrodes 3a, 4a forming the detection electrodes 3, 4, and the lead electrodes 31, 41 are arranged so as to face each other with a relatively thin ceramic green sheet 2a interposed therebetween. The uppermost layer of the sensor element 1 is assumed to be the ceramic green sheet of the sensor element 1 located at the uppermost side of the drawing of FIG. 5. For example, two relatively thick ceramic green sheets 2b are arranged respectively in the uppermost layer or the lowermost layer opposing the uppermost layer of the sensor element 1. The thickness of the ceramic green sheet 2a corresponds to the distance between the detection electrodes 3 and 4, and is set so as to provide a desired inter-electrode distance. The terminal electrodes 32 and 42 are formed on the surface of the ceramic green sheets 2b serving as the uppermost layer of the insulating substrate 2.

At the lowermost layer of the sensor element 1, a heater electrode 61 and lead electrodes 62, 63 are embedded between the two ceramic green sheets 2b to form a heater part 6. Terminal electrodes 64 and 65 for the heater part 6 are formed on the surface of the ceramic green sheet 2b serving as the lowermost layer, at the end opposing the heater electrode 61. The heater electrode 61 is located at a position corresponding to the positions where the electrodes 3a, 4a forming the detection electrodes 3, 4 are formed, and it is capable of heating the entire detection face 11. The particulate matter detection sensor energizes the heater part 6 upon operation of the sensor element 1 to remove moisture and PM adhering to the surface of the detection face 11, thereby preventing detection errors.

Figure 6:
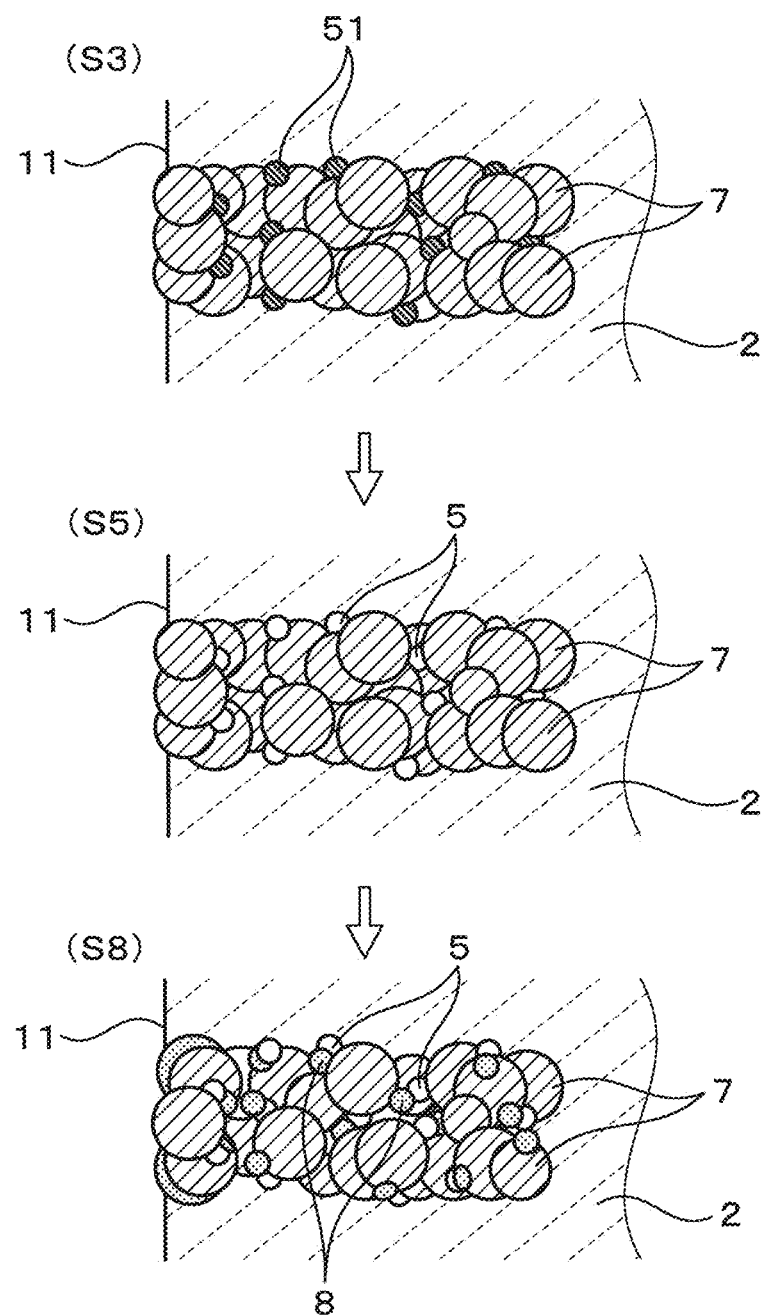
FIG. 6 is a schematic cross-sectional view showing the change in the configuration of the detection electrode of the sensor element through the manufacturing process and after the manufacturing according to the first embodiment.

Such a laminated type sensor element 1 is manufactured through a sheet forming step S1, an electrode printing step S2, a lamination step S3, a cutting step S4, and a firing step S5. In the sheet forming step S1, a plurality of ceramic green sheets 2a and 2b are formed. In the electrode printing step S2, the detection electrodes 3 and 4 are printed. In the lamination step S3, the plurality of ceramic green sheets 2a and 2b are laminated. In the cutting step S4, the laminate obtained in the lamination step S3 is cut into a given shape. In the firing step S5, the laminate is fired. The obtained sensor element is further subjected to a processing step S6 and an assembling step S7, and finally becomes the sensor element 1 for a PM detection sensor. With reference to FIG. 6, the following description will discuss in detail the manufacturing process of the sensor element 1.

In the sheet forming step S1, an organic solvent and an organic binder are added to a powder of a ceramic material such as alumina to form a slurry. Then, the slurry is formed into a sheet having a predetermined thickness by a known doctor blade method, followed by drying to obtain ceramic green sheets 2a, 2b. Next, in electrode printing step S2, the electrodes 3a, 4a forming the detection electrode 3 or the detection electrode 4 are formed on the surface of the ceramic green sheet 2a.

The materials of the electrodes 3a and 4a may be the alloy particles 7 of Pt—Rh or the like, an aggregate such as alumina, void forming particles for forming the granular voids 5, for example, resin beads, and a paste electrode material. The paste electrode material is obtained by adding and mixing an organic solvent and an organic binder. The electrodes 3a, 4a can be formed to have a predetermined pattern, for example, by screen printing. Here, the electrodes 3a, 4a forming the detection electrodes 3, 4 are made of rectangular electrode films having the same pattern, but it is also possible to adopt two kinds of electrode patterns having symmetrical shapes.

Here, the resin beads, which are void forming particles, are spherical particles which burn out by the firing to form granular voids 5 around the alloy particles 7. The resin beads melt and decompose at a temperature (for example, about 400° C.) equivalent to that of the organic binder. Specifically, for example, resin beads of a resin material having good solvent resistance retain their form without being dissolved in the solvent used for the paste electrode material. Thus, it is possible to easily adjust the void diameter and the number of voids.

Similarly, a plurality of electrodes is formed on the surfaces of ceramic green sheets 2b to have predetermined patterns, for example, by screen printing. The plurality of electrodes are the lead electrodes 31, 41, the terminal electrodes 32, 42, the heater electrode 61, the lead electrodes 62, 63, or the terminal electrodes 64, 65 for the heater part 6. It should be noted that the ceramic green sheets 2a and 2b are cut into a given size in advance. At predetermined positions of the ceramic green sheets 2a and 2b, through holes are provided to connect the lead electrodes 31 and 41 to the terminal electrodes 32 and 42, and the lead electrodes 62 and 63 to the terminal electrodes 64 and 65, respectively. Similar electrode materials are filled in these through holes in the electrode printing step S2.

In the lamination step S3, the ceramic green sheets 2a and 2b are laminated in a predetermined order, followed by pressing and pressure bonding to form a laminate. In the cutting step S4, the obtained block-like laminate is cut conforming to the shape of the sensor element 1 with a cutting machine or by dicing. In the firing step S5, after degreasing, the laminate is fired at a temperature that is equal to or higher than the sintering temperature of the ceramic material (for example, 1450° C.).

As shown in FIG. 6, in the laminate obtained by the lamination step S3, the resin beads 51 which are void forming particles are dispersed in the electrode films forming the detection electrodes 3, 4. In the firing step S5, when this laminate is fired, the resin beads 51 melt and decompose in the process of heating. Once the resin beads have burnt out, the granular voids 5 are formed. The number of the granular voids 5 contained in the detection electrodes 3, 4 can be adjusted according to the mixing amount of the resin beads 51. The size of the granular voids 5 can be adjusted according to the particle diameter of the resin beads 51.

In the processing step S6, by grinding the detection face 11 of the obtained fired body to expose the detection electrodes 3, 4, the sensor element 1 is obtained. In the assembling step S7, the sensor element 1 is further held in a cylindrical housing (not shown) for attachment, and covered with a covering provided with hole to form a particulate matter detection sensor.

The sensor element 1 thus manufactured is used for a particulate matter detection sensor placed at, for example, the exhaust gas outlet side of an exhaust gas purification filter provided in the exhaust passage of an internal combustion engine. The sensor element 1 detects the PM in the combustion exhaust gas that has passed through the exhaust gas purification filter. It is also possible to use the sensor element 1 for a particulate matter detection sensor placed at the exhaust gas inlet side of the exhaust gas purification filter. In such case, it can detect the PM in the combustion exhaust gas that has not yet passed through the exhaust gas purification filter.

The exhaust gas purification filter may be a diesel particulate filter (i.e., DPF) or a gasoline particulate filter (i.e., GPF). The particulate matter detection sensor including the sensor element 1 may be used for detecting the PM contained in the combustion exhaust gas exhausted from a diesel engine. Further, it may be used for detecting the PM contained in the combustion exhaust gas exhausted from a gasoline engine.

S8 is a step of PM detection and PM removal, and after this PM detection, a process of removing deposited PM is repeated. At this time, as shown in FIG. 6, the detection electrodes 3, 4, exposed at the detection face 11 and opposed to each other with the insulating substrate 2 interposed therebetween, are exposed to the combustion exhaust gas flowing through the exhaust passage. When PM is detected, a predetermined voltage is applied between the detection electrodes 3, 4 to form an electrostatic field. Then, PM is attracted to and accumulated on the surface of the detection face 11.

As shown in the top illustration of FIG. 7, when the PM detection is completed, the PM particles connect the detection electrodes 3, 4 and provide conductivity. From this state, in order to remove the PM, the heater part 6 of the sensor element 1 is energized to heat the surface of the detection face 11 to a temperature equal to or higher than the temperature at which the PM can burn (for example, 750°

C.). As a result, as shown in the middle illustration of FIG. 7, the PM containing carbon as a main component burns and $CO_2$ is released, and as shown in the bottom illustration of FIG. 7, the PM is removed from the detection face 11.

The heating temperature for the PM removal in S8 is a temperature that causes oxidization of the metal such as Rh included in the Pt—Rh alloy constituting the detection electrodes 3, 4. Thus, as shown in FIG. 6, a metal oxide 8 ($Rh_2O_3$) is produced in the detection electrodes 3, 4 by Rh being oxidized. At this time, since $Rh_2O_3$ is generated not only at the detection face 11 exposed to the gas to be measured but also at those parts in contact with the granular voids 5 serving as oxygen donors, segregation of $Rh_2O_3$ does not occur. That is, since the granular voids 5 are appropriately dispersed inside the detection electrodes 3, 4, the decrease in the Rh concentration due to formation of $Rh_2O_3$ also occurs throughout the detection electrodes 3, 4. In addition, movement of Rh to compensate for the decrease in Rh concentration is suppressed. Thus, the surfaces of the detection electrodes 3, 4 are kept flush with each other at the detection face 11, and variation in the distance between the electrodes can be suppressed.

Second Embodiment

Figure 8:
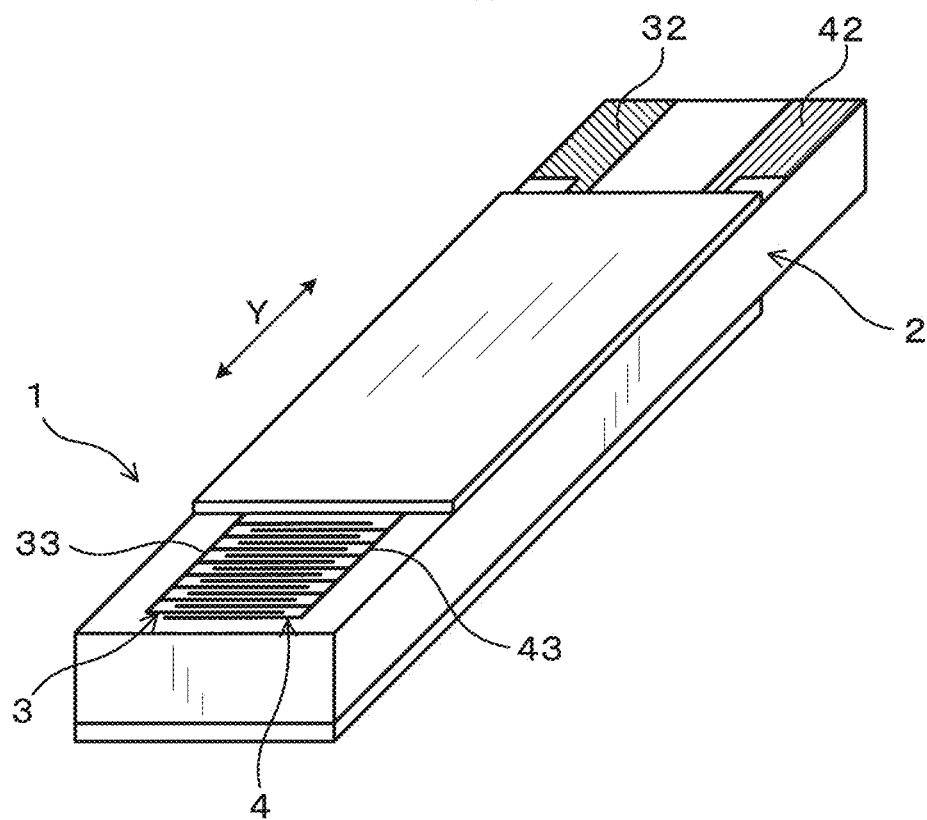
FIG. 8 is an overall perspective view of a sensor element according to a second embodiment.
Figure 9:
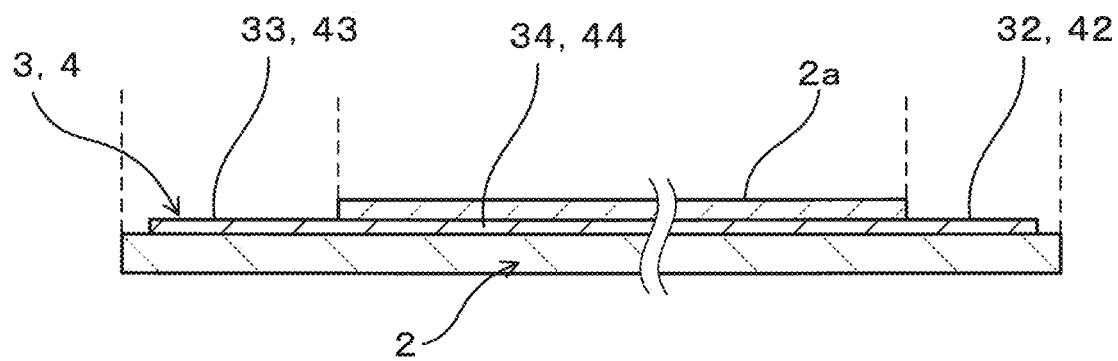
FIG. 9 is a cross-sectional view of the sensor element in the longitudinal direction according to the second embodiment.
Figure 10:
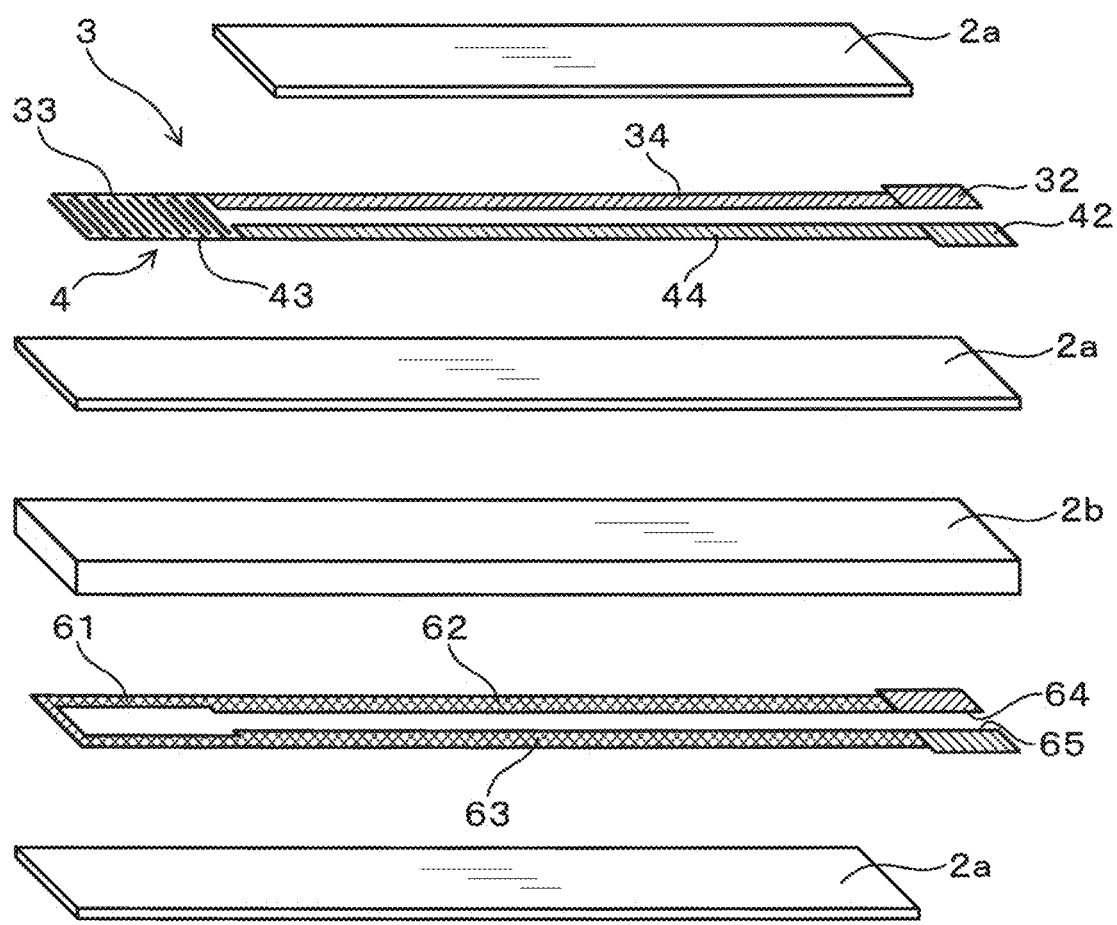
FIG. 10 is an exploded view of an overall configuration of the sensor element according to the second embodiment.

In the first embodiment, one end face of the laminated type sensor element 1 serves as the detection face 11. In addition, the sensor element 1 has a laminated type electrode structure in which electrode films of the plurality of detection electrodes 3 and 4 are embedded in the insulating substrate 2 like layers. A part of the plurality of pairing detection electrodes 3 and 4 is referred to as a first group and the remaining plurality of pairing detection electrodes 3 and 4 are referred to as a second group. As shown in FIGS. 8 to 10 as the second embodiment, in the sensor element 1, it can also be a printed type electrode structure in which the first group is printed on the surface that is going to be the detection face 11 of the insulating substrate 2, and the second group is embedded. The basic configuration of the sensor element 1 is the same as that of the first embodiment, and mainly the differences from the first embodiment will be described below.

In this embodiment, the sensor element 1 has an insulating substrate 2 having a flat cuboid shape. A part of the upper face of the insulating substrate 2 (that is, the closer part of the upper face of the insulating substrate 2 shown in FIG. 8, the left part of the upper face of the insulating substrate 2 shown in FIGS. 9 and 10) serves as the detection face 11. A heater section 6 is provided at the side opposing the detection face 11. The pair of detection electrodes 3, 4 are composed of detection parts 33, 43 composed of a pair of comb-like electrodes arranged on the detection face 11, and lead parts 34, 44. The lead parts 34, 44 are embedded inside the insulating substrate 2. Terminal electrodes 32, 42 are formed on a part of the upper face of the insulating substrate 2 (that is, the rear part of the upper face in FIG. 8, the right part of the upper face in FIGS. 9 and 10). The lead parts 34, 44 extending along the longitudinal direction Y of the insulating substrate 2 connect the detection parts 33, 43 and the terminal electrodes 32, 42. The detection parts 33, 43 are comb-like electrodes each having a plurality of linear electrodes. The plurality of linear electrodes are connected with each other at one end and are connected to the lead parts 34, 44.

As shown in FIG. 10, for example, the insulating substrate 2 is formed by laminating ceramic green sheets 2a, 2b with different thicknesses. A plurality of ceramic green sheets 2a having a relatively thin sheet thickness are laminated with a relatively thick ceramic green sheet 2b interposed therein. The pair of detection electrodes 3, 4 and the terminal electrodes 32, 42 are formed on the surface of the ceramic green sheet 2a located right above the ceramic green sheet 2b. The ceramic green sheet 2a covering the upper surfaces of the lead parts 34 and 44 is placed at the uppermost layer of the insulating substrate 2.

In the present embodiment as well, it is possible to form the detection electrodes 3, 4 using alloy particles 7 of Pt—Rh or the like, an aggregate such as alumina, and an electrode material, by screen printing or the like so as to have a predetermined pattern. The electrode material includes void forming particles.

Between the ceramic green sheet 2a at the lowermost layer of the sensor element 2 and the ceramic green sheet 2b, a heater electrode 61 and lead electrodes 62, 63 which form a heater part 6 are embedded. These electrodes are connected to terminal electrodes 64, 65 exposed at the lower face of the ceramic green sheet 2b. The heater electrode 61, lead electrodes 62, 63, and terminal electrodes 64, 65 can be formed using a normal electrode material by screen printing or the like so as to have a predetermined pattern.

The detection electrodes 3, 4 the terminal electrodes 32, 42, the heater electrode 61, the lead electrodes 62, 63, and the terminal electrodes 64, 65 were printed on these ceramic green sheets 2a, 2b constituting the insulating substrate 2. Then, the ceramic green sheets 2a and 2b are laminated in a given order and are integrally fired, whereby the sensor element 1 is formed.

In the sensor element 1 of the present embodiment, the lead parts 34, 44 constituting a part of the detection electrodes 3, 4 are embedded in the insulating substrate 2. In such configuration as well, advantageous effects similar to those of the first embodiment can be obtained by adjusting the granular voids 5 present in the detection electrodes 3, 4 to be within the above-mentioned predetermined range. That is, it is possible to prevent metal such as Rh serving as an electrode material diffusing from the lead parts 34, 44 to the detection parts 33, 43. The detection parts 33, 43 are exposed at the detection face 11. It is possible to suppress variation of the inter-electrode distance upon heating in the removal process after PM detection.

Experimental Example 1

Next, the sensor element 1 of the first embodiment was fabricated by the method described above, and the variation in the electrode resistance of the detection electrodes 3, 4 was examined by a durability test. For the detection electrodes 3, 4, an electrode material was used. The electrode material was obtained by adding void forming particles made of resin beads to alloy particles 7 of a Pt—Rh alloy, an aggregate of alumina, and an electrode paste. The electrode paste is formed by mixing and kneading an organic solvent with an organic binder. The alloy particles 7 were prepared by mixing an acid solution containing Pt ions and Rh ions, and causing a reduction reaction with a reduction agent. At this time, the amounts of Pt ions and Rh ions were adjusted to vary the percentage by mass of Pt and Rh in the range of Pt: 98 mass % to 69 mass %, Rh: 2 mass % to 31 mass %. This is the ratio on the assumption that the total amount of Pt and Rh is 100 mass %.

Further, the amount of the resin beads used as void forming particles added to the electrode paste is varied. By doing so, the number of the granular voids 5 per unit volume can be varied in the range of 3/100 µm$^3$ to 79/100 µm$^3$ as shown in Table 1 (that is, Examples 1 to 11, Comparative Examples 1 and 2). Here, the number of the granular voids 5 is a value converted into number per unit volume by making a three-dimensional image of the detection electrodes 3, 4 and observing the granular voids 5 contained therein. For the observation and creation of a three-dimensional image, a three-dimensional scanning electron microscope (hereinafter referred to as 3D-SEM) and an energy dispersive X-ray spectrometer (hereinafter referred to as EDX) were used.

Figure 11:
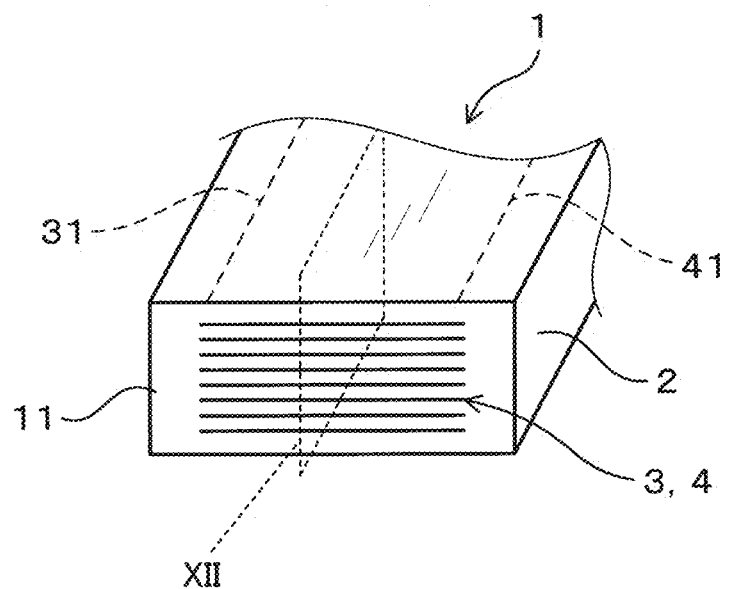
FIG. 11 is an enlarged perspective view of a part of a sensor element showing a region in the vicinity of a detection face observed by a scanning electron microscope according to Experimental Example 1.
Figure 12:
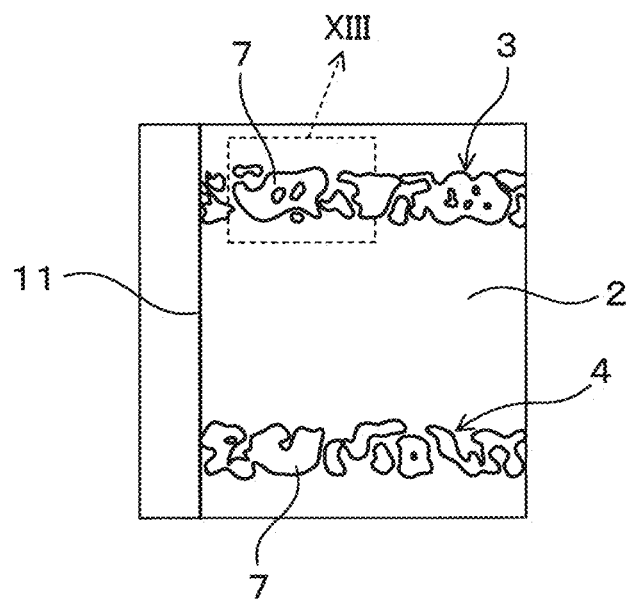
FIG. 12 is a schematic view of a cross-sectional structure of a region XII of FIG. 11 which is a cross section of the sensor element in the vicinity of the detection face observed with a scanning electron microscope according to Experimental Example 1.
Figure 13:
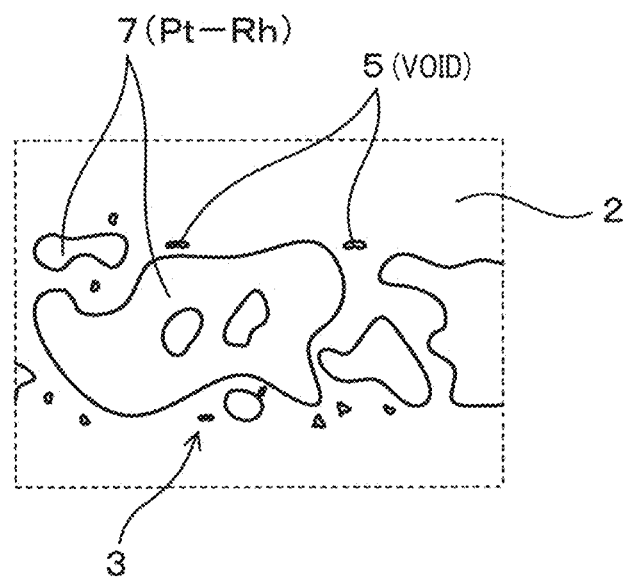
FIG. 13 is a schematic enlarged view of a cross-sectional structure of a region XIII of FIG. 12 which is a cross section of the sensor element in the vicinity of the detection face observed with a scanning electron microscope according to Experimental Example 1.

Table 1 shows the number of granular voids 5 per unit volume and the ratio of Pt and Rh for the sensor elements 1 of Examples 1 to 11 and Comparative Examples 1 and 2, together with the measurement results of the void diameter and void dispersion degree. Here, the void diameter is an average diameter (unit: µm) of the granular voids 5, and is an average value obtained by measuring the particle diameters of 30 granular voids 5 using a three-dimensional image obtained by 3D-SEM, EDX. As for the void dispersion degree, for example, as shown in FIGS. 11 to 13, the electrode cross section in the current flow direction was observed using the SEM images of the detection electrodes 3 and 4. The electrode cross section was divided into four in the laminating direction X (that is, the direction orthogonal to the current flow direction). Then, it was calculated as the ratio of the number of voids in the end parts to the total number of voids (that is, the number of voids in the two end parts/the total number of voids).

Figure 14:
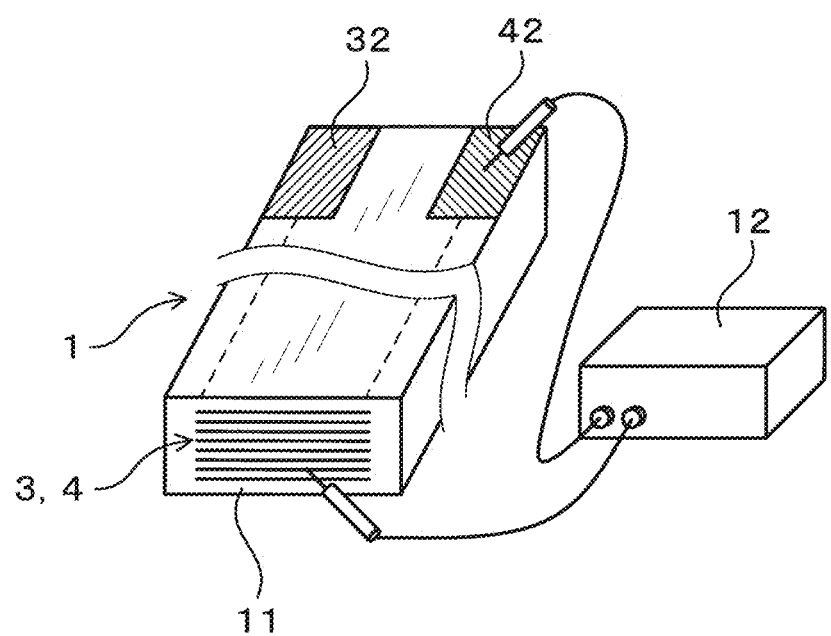
FIG. 14 is a schematic view illustrating the method of measuring the electrode resistance change ratio of the sensor element according to Experimental Example 1.

In the durability test, PM detection and PM removal were repeated by the method shown in S8 of FIG. 6, and the electrode resistances before and after the durability test were measured. Specifically, using the heater part 6, heating was performed so that the temperature of the detection face 11 of the sensor element 1 reaches 750° C. The durability time (heating time) was 730 hours in total. As shown in FIG. 14, using a known digital multimeter 12, the electrode resistance was measured by bringing probes into contact with the detection electrode 3, 4 of the sensor element 1 and the terminal electrode 32, 42 (for example, one of the detection electrodes 4 and the terminal electrode 42 in this case). The electrode resistance change ratio (unit: %) was calculated by the following formula. The results are shown in Table 1.

Electrode resistance change ratio=(Electrode resistance after endurance/initial electrode resistance)×100

The durability was rated good (○) when the electrode resistance change ratio was below 10×100%, acceptable (Δ) when it was 10×100% to 40×100%, unacceptable (×) when it was higher than 40×100%.

In Table 1, in all of Examples 1 to 11 where the number of the granular voids 5 is in the range of 3/100 µm$^3$ to 50/100 µm$^3$, good durability was obtained. Further, from the observation results of the three-dimensional image, the metal oxide 8 was generated inside the detection electrodes 3 and 4 by the oxidation of Rh. About 90% of the metal oxide 8 was found to be present in the vicinity of the granular voids 5. On the other hand, in Comparative Examples 1 and 2 where the number of the granular voids 5 exceeds 70/100 µm$^3$, the change in the electrode resistance is larger. When the number of the granular voids 5 increases, the amount of the metal oxide 8 produced by oxygen donation from the granular voids 5 increases. This presumably promotes the increase in the electrode resistance.

Experimental Example 2

Sensor elements 1 were prepared under the following conditions in the same manner as in Experimental Example

TABLE 1

| EXAMPLE No. COMPARATIVE EXAMPLE No. | NUMBER OF VOIDS (VOIDS/100 µm$^3$) | Pt (MASS %) | Rh (MASS %) | VOID DIAMETER (µm) | VOID DISPERSION DEGREE (—) | ELECTRODE RESISTANCE CHANGE RATIO [%] | DURABILITY |
|---|---|---|---|---|---|---|---|
| EXAMPLE 1 | 7 | 98 | 2 | 0.9 | 0.68 | 0.9 × 10$^2$ | ○ |
| EXAMPLE 2 | 3 | 89 | 11 | 1 | 0.69 | 3 × 10$^2$ | ○ |
| EXAMPLE 3 | 15 | 98 | 2 | 1 | 0.78 | 0.9 × 10$^2$ | ○ |
| EXAMPLE 4 | 14 | 89 | 11 | 1.2 | 0.65 | 1.1 × 10$^2$ | ○ |
| EXAMPLE 5 | 9 | 69 | 31 | 0.8 | 0.82 | 3 × 10$^2$ | ○ |
| EXAMPLE 6 | 19 | 98 | 2 | 0.9 | 0.7 | 0.8 × 10$^2$ | ○ |
| EXAMPLE 7 | 28 | 89 | 11 | 0.8 | 0.67 | 0.9 × 10$^2$ | ○ |
| EXAMPLE 8 | 21 | 69 | 31 | 1.1 | 0.73 | 1.5 × 10$^2$ | ○ |
| EXAMPLE 9 | 45 | 98 | 2 | 1 | 0.71 | 2.3 × 10$^2$ | ○ |
| EXAMPLE 10 | 48 | 89 | 11 | 0.8 | 0.82 | 3.8 × 10$^2$ | ○ |
| EXAMPLE 11 | 49 | 69 | 31 | 1.1 | 0.73 | 7.0 × 10$^2$ | ○ |
| COMPARATIVE EXAMPLE 1 | 79 | 98 | 2 | 1.1 | 0.72 | 46 × 10$^2$ | x |
| COMPARATIVE EXAMPLE 2 | 76 | 69 | 31 | 1.3 | 0.68 | 114 × 10$^2$ | x |

As shown in FIGS. 12 and 13, from the observation results of the SEM image of the detection electrodes 3, 4, it was confirmed that a plurality of granular voids 5 were formed around the alloy particles 7 of a Pt—Rh alloy.

1, which will be referred to as Examples 12 to 15 and Comparative Examples 3 and 4. (1) The number of the granular voids 5 is in the range of 19/100 µm$^3$ to 28/100 µm$^3$, (2) the ratio of Pt and Rh is in the range of Pt: 100 mass % to 39 mass %, Rh: 0 mass % to 61 mass %. For these Examples 12 to 15 and Comparative Examples 3 to 5, the same durability test as with Experimental Example 1 was carried out. The measurement results of the change in the electrode resistance of the detection electrodes 3, 4 are shown in Table 2 together with the void diameter and the void dispersion degree.

(d), when PM is detected again, the actual inter-electrode distance becomes longer than the initial state. In such case, the detection time until the detected current reaches the specified value becomes longer as indicated by the dotted line B, as compared with the detected current characteristic A in the initial state shown by the solid line in FIG. 16. When

TABLE 2

| EXAMPLE No. COMPARATIVE EXAMPLE No. | NUMBER OF VOIDS (VOIDS/100 μm³) | Pt (MASS %) | Rh (MASS %) | VOID DIAMETER (μm) | VOID DISPERSION DEGREE (—) | ELECTRODE RESISTANCE CHANGE RATIO [%] | DURABILITY |
|---|---|---|---|---|---|---|---|
| COMPARATIVE EXAMPLE 3 | 25 | 100 | 0 | 0.9 | 0.72 | N/A | x |
| EXAMPLE 12 | 20 | 99.5 | 0.5 | 1 | 0.71 | $3 \times 10^2$ | o |
| EXAMPLE 13 | 19 | 98 | 2.2 | 0.9 | 0.7 | $0.8 \times 10^2$ | o |
| EXAMPLE 14 | 28 | 89 | 11 | 0.8 | 0.67 | $0.9 \times 10^2$ | o |
| EXAMPLE 15 | 21 | 69 | 31 | 1.1 | 0.73 | $1.5 \times 10^2$ | o |
| COMPARATIVE EXAMPLE 4 | 26 | 51 | 49 | 1.2 | 0.69 | $42 \times 10^2$ | x |
| COMPARATIVE EXAMPLE 5 | 24 | 39 | 61 | 1.1 | 0.72 | $200 \times 10^2$ | x |

In Table 2, regarding Comparative Example 3, the detection electrodes 3 and 4 gradually dissipate from the detection face 11 of the sensor element 1 toward the inside of the insulating substrate, and eventually disappear. The electrode resistance after the durability test was therefore unable to be measured. In Comparative Example 3, Pt is not blended with Rh. As the ratio of Rh to Pt increases, the electrode resistance change ratio increases. In Comparative Examples 4 and 5 where the content of Rh exceeds 40 mass %, the electrode resistance after the durability test increased, and sufficient durability could not be obtained.

Figure 15:
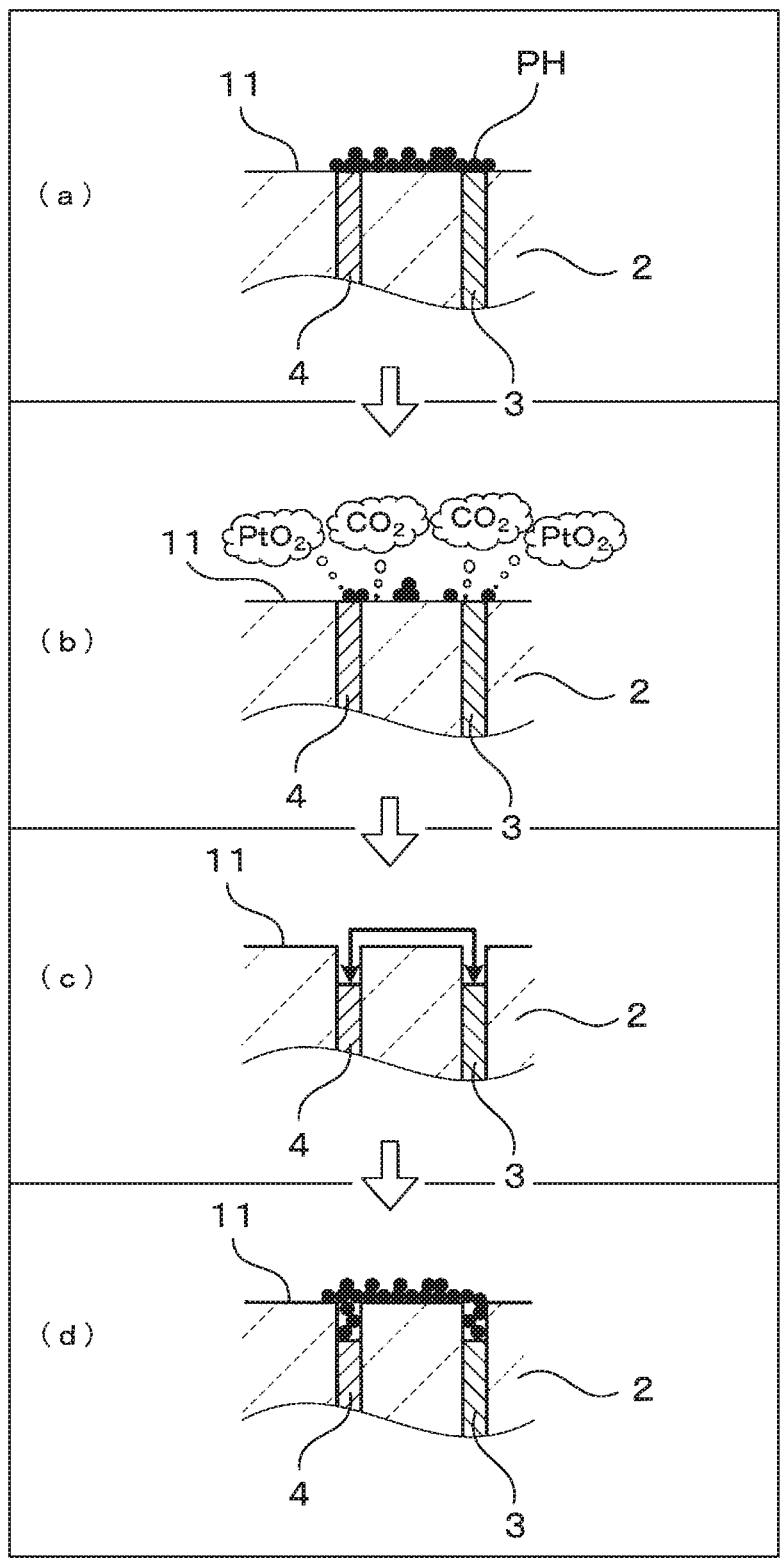
FIG. 15 is a schematic view showing the change in the electrode structure of a conventional sensor element before and after a durability test.

As shown in FIG. 15, in Comparative Example 3 where Rh was not added to Pt, after the PM detection shown in (a), Pt turns into $PtO_2$ and evaporates in step (b). The step of (b) is a step of heating the PM attached to the detection face 11 of the sensor element 1 to a high temperature in order to oxidize and remove it. Thus, upon completion of the PM removal shown in (c), the detection electrodes 3, 4 gradually dissipate from the detection face 11 toward the inside of the insulating substrate, and eventually disappear. In the step of this is repeated, the detection time becomes longer as indicated by the dotted line C and exceeds the specified time t, making detection impossible.

Experimental Example 3

Sensor elements 1 were fabricated under the following conditions in the same manner as with Experimental Example 1 to obtain Examples 16 to 21. (1) The number of the granular voids 5 of Pt and Rh is in the range of 19/100 μm³ to 28/100 μm³, (2) the size of the granular voids 5 is in the range of 0.3 μm to 1.1 μm, (3) the degree of void dispersion is in the range of 0.67 to 0.79. The measurement results of the change in the electrode resistance of the detection electrodes 3, 4 obtained by carrying out a similar durability test on Examples 16 to 21 are shown in Table 3 together with the ratio of Pt and Rh.

TABLE 3

| EXAMPLE No. | NUMBER OF VOIDS (VOIDS/100 μm³) | Pt (MASS %) | Rh (MASS %) | VOID DIAMETER (μm) | | VOID DISPERSION DEGREE (—) | ELECTRODE RESISTANCE CHANGE RATIO [%] | DURABILITY |
|---|---|---|---|---|---|---|---|---|
| EXAMPLE 16 | 19 | 98 | 2.2 | ≤0.5 | 0.5 | 0.71 | $0.9 \times 10^2$ | o |
| EXAMPLE 17 | 22 | 89 | 11 | | 0.4 | 0.79 | $1.1 \times 10^2$ | o |
| EXAMPLE 18 | 23 | 69 | 31 | | 0.3 | 0.73 | $3 \times 10^2$ | o |
| EXAMPLE 19 | 19 | 98 | 2.2 | ≤1.5 | 0.9 | 0.7 | $0.8 \times 10^2$ | o |
| EXAMPLE 20 | 28 | 89 | 11 | | 0.8 | 0.67 | $0.9 \times 10^2$ | o |
| EXAMPLE 21 | 21 | 69 | 31 | | 1.1 | 0.73 | $1.5 \times 10^2$ | o |
| EXAMPLE 22 | 21 | 98 | 2.2 | ≤2.5 | 2.5 | 0.68 | $0.7 \times 10^2$ | o |
| EXAMPLE 23 | 22 | 89 | 11 | | 2.3 | 0.71 | $1.0 \times 10^2$ | o |
| EXAMPLE 24 | 23 | 69 | 31 | | 2.3 | 0.65 | $2.3 \times 10^2$ | o |
| EXAMPLE 25 | 25 | 98 | 2.2 | ≤5.0 | 4.8 | 0.54 | $3.1 \times 10^2$ | o |

In Table 3, for all of Examples 16 to 21, which have a degree of void dispersion above 0.50 when the size of the granular voids 5 and the content of Rh are in the above ranges, good durability was obtained.

Experimental Example 4

Sensor elements 1 were prepared under the following conditions in the same manner as in Experimental Example 1, which will be referred to as Examples 22 to 30. (1) The number of the granular voids 5 of Pt and Rh is in the range of 19/100 μm³ to 28/100 μm³, (2) the size of the granular voids 5 is in the range of 0.9 μm to 1.2 μm, (3) the degree of void dispersion is in the range of 0.55 to 0.95. The measurement results of the change in the electrode resistance of the detection electrodes 3, 4 obtained by carrying out a similar durability test on Examples 22 to 30 are shown in Table 4 together with the ratio of Pt and Rh.

heated at a temperature of 900° C. for 250 hours. Then, the distance between the detection electrodes 3 and 4 at the detection face 11 was measured, and the change ratio from the distance before the high temperature durability test was calculated. The samples were rated good when the change ratio was 0%, acceptable when the change ratio was higher than 0% and 5% or lower, and unacceptable when the change ratio exceeded 5%.

As a result, the sensor element 1 having with 100 mass % Pt had a change ratio exceeding 5% and was rated as unacceptable. On the other hand, the sensor elements 1 which used alloys of Pt and Rh, Ru, Ir, or Os each had a change ratio of 0%, and good results were obtained. The sensor element 1 which used the alloy of Pt and Pd had a change ratio of 5% or less, which is slightly inferior to the other metals, but still the advantageous effect of suppressing volatilization of Pt was confirmed.

TABLE 4

| EXAMPLE No. | NUMBER OF VOIDS (VOIDS/100 μm³) | Pt (MASS %) | Rh (MASS %) | VOID DIAMETER (μm) | VOID DISPERSION DEGREE (—) | | ELECTRODE RESISTANCE CHANGE RATIO [%] | DURABILITY |
|---|---|---|---|---|---|---|---|---|
| EXAMPLE 26 | 25 | 98 | 2 | 0.9 | 0.85≤ | 0.95 | $0.7 \times 10^2$ | ○ |
| EXAMPLE 27 | 24 | 89 | 11 | 0.9 | | 0.91 | $1.0 \times 10^2$ | ○ |
| EXAMPLE 28 | 22 | 69 | 31 | 1 | | 0.86 | $1.3 \times 10^2$ | ○ |
| EXAMPLE 29 | 19 | 98 | 2 | 0.9 | 0.65≤ | 0.7 | $0.8 \times 10^2$ | ○ |
| EXAMPLE 30 | 28 | 89 | 11 | 0.8 | | 0.67 | $0.9 \times 10^2$ | ○ |
| EXAMPLE 31 | 21 | 69 | 31 | 1.1 | | 0.73 | $1.5 \times 10^2$ | ○ |
| EXAMPLE 32 | 23 | 98 | 2 | 1.2 | 0.55≤ | 0.57 | $1.1 \times 10^2$ | ○ |
| EXAMPLE 33 | 24 | 89 | 11 | 1 | | 0.55 | $1.1 \times 10^2$ | ○ |
| EXAMPLE 34 | 21 | 69 | 31 | 1 | | 0.58 | $1.7 \times 10^2$ | ○ |
| EXAMPLE 35 | 25 | 98 | 2 | 3.9 | 0.45≤ | 0.47 | $10 \times 10^2$ | Δ |
| EXAMPLE 36 | 23 | 69 | 31 | 4.1 | | 0.51 | $13 \times 10^2$ | Δ |

In Table 4, regarding Examples 22 to 30 whose size of the granular voids 5 are 1.5 μm or less when the void dispersion degree and the content of Rh are in the above ranges, good durability was obtained.

Experimental Example 5

Next, the advantageous effect on the volatilization of Pt was evaluated using alloys of Pt and the following metals instead of an alloy of Pt and Rh as the electrode material of the detection electrodes 3, 4. The metal used with Pt here is at least one metal selected from Rh, Ru, Ir, Os and Pd. Sensor elements 1 were fabricated in the same manner as in Experimental Example 1, using alloys of Pt and these metals, an aggregate, and an electrode paste for the detection electrodes 3 and 4. The aggregate is composed of alloy particles 7 with Pt: other metal=98 mass %: 2 mass %, and alumina. The electrode paste is formed by mixing and kneading an organic solvent with an organic binder. For comparison, a sensor element 1 was fabricated in the same manner using an electrode material having 100 mass % Pt.

Figure 18:
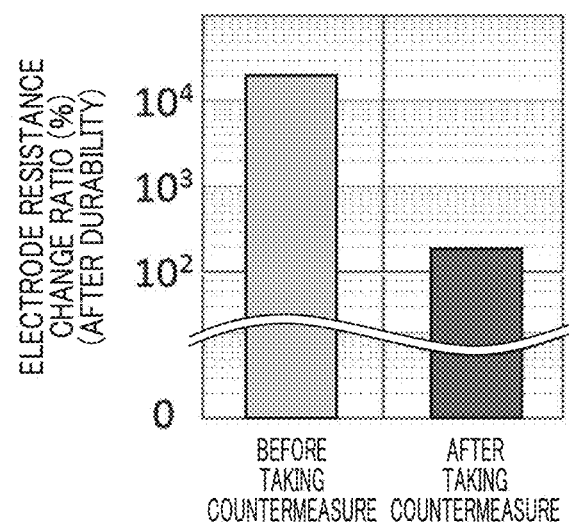
FIG. 18 shows, in comparison with a conventional sensor element, the measurement results of the electrode resistance change ratio of the sensor element after the durability test according to Experimental Example 5, where Rh is chosen for the alloy among the metals shown with regard to Experimental Example 5 as a representative example.

The obtained sensor elements 1 were subjected to a high temperature durability test. First, each sensor element 1 was In FIG. 18, "before taking countermeasure" indicates a conventional sensor element where resin beads are not added to the electrode material. In FIG. 18, "after taking countermeasure" indicates a sensor element 1 manufactured by adding resin beads to the electrode material as in Experimental Example 1. Further, "before taking countermeasure" indicates a sensor element that uses an alloy of Pt and Rh of the above test examples. The number of the granular voids 5 of the sensor element 1 after taking the countermeasure was adjusted to be in the range of 19/100 μm³ to 28/100 μm³. As with Experimental Example 1, a durability test was conducted to measure the electrode resistance change ratio. As shown in FIG. 17, it was confirmed that the granular voids 5 were formed inside the electrodes of the sensor element 1 as compared with the conventional element. As a result, in Example 31 where the granular voids 5 were formed, the electrode resistance change ratio became small and the durability was improved.

In the sensor element before taking the countermeasure shown in FIG. 18, it was found that metal oxide is generated by oxidation of Rh on the surface of the detection face exposed to the atmosphere. The formation of this metal oxide reduces the Rh concentration in the vicinity of the detection face. Rh diffuses from the inside of the detection electrodes toward the detection face. As a result, Rh is further oxidized, causing segregation of the metal oxide. Presumably, thus, the electrode resistance in the vicinity of the detection face increases, which leads to an increase in the electrode resistance as a whole.

On the other hand, in case of the sensor element 1 after taking the countermeasure shown in FIG. 18, the metal oxide 8 is generated not only on the detection face 11 but also inside the electrodes due to oxygen donation from the granular voids 5 inside the electrodes. Thus, the difference in Rh concentration in the electrode alloy between the outermost surface and the inside of the detection electrodes 3, 4 decreases, and the amount of Rh diffused to the outermost surface of the electrodes decreases. As a result, the amount of metal oxide 8 formed on the outermost surface of the electrodes exposed at the detection face 11 decreases, and the increase ratio of the resistance at the outermost surface of the electrodes decreases. This makes it possible to suppress the volatilization of Pt in the detection electrodes 3, 4, and also to suppress the increase ratio of the resistance of the entire detection electrodes 3, 4.

The electrode for a sensor element and the sensor element 1 according to the present disclosure are not limited to the above-described embodiments and examples, and various modifications may be made within a range that does not exceed the spirit of the present disclosure. For example, in the above embodiments, an example of application to a particulate matter detection sensor for detecting a particulate matter contained in a combustion exhaust gas of an internal combustion engine has been described. However, the gas to be measured containing a particulate matter is not limited to a combustion exhaust gas, and further, it may be used for applications other than failure diagnosis of a post-processing apparatus such as a DPF. Furthermore, it can also be applied to a sensor element having a similar detection electrode structure but is used to detect substances other than particulate matter.

In addition, the sensor element 1 is not limited to the ones described in the above embodiment, and may have any configuration as long as it has, on the surface of the insulating substrate 2, a detection face 11 where a part of the detection electrodes 3, 4 is exposed. For example, the shapes and other properties of the insulating substrate 2 and the detection electrodes 3, 4 of the sensor element 1 can be changed as appropriate.

REFERENCE SIGNS LIST

1 . . . Sensor element
11 . . . Detection face
2 . . . Insulating substrate
3, 4 . . . Detection electrode
5 . . . Granular void
7 . . . Alloy particle (i.e., alloy)
8 . . . Metal oxide

The invention claimed is:

1. A sensor element that detects a specific substance in a gas to be measured, comprising:
    an insulating substrate having a detection face to which the specific substance adheres; and
    a pair of detection electrodes with different polarities, a part of each detection electrode being exposed at the detection face in such a manner that the detection electrodes face each other, and a remaining part thereof being embedded in the insulating substrate, wherein
    each detection electrode comprises an alloy of Pt and at least one metal selected from a group consisting of Rh, Ru, Ir, Os, and Pd, and granular voids dispersed among the alloy, the content of the metal in the alloy is 40 mass % or less, and the number of the granular voids per unit volume of the detection electrodes is $3/100$ $\mu m^3$ to $50/100$ $\mu m^3$, and
    the pair of detection electrodes each comprises a plurality of electrodes, and the plurality of electrodes are laminated at predetermined intervals inside the insulating substrate so that the polarity differs alternately, and in a lamination direction of the detection electrodes, more granular voids are provided in both end parts of the detection electrodes than in a central part thereof.

2. The sensor element according to claim 1, wherein the metal is Rh, and the Rh content in the alloy is 2 mass % to 30 mass %.

3. The sensor element according to claim 1, wherein the granular voids have an average particle diameter of 1.5 μm or less.

4. The sensor element according to claim 1, wherein the specific substance is particulate matter.

5. The sensor element according to claim 1, wherein a void dispersion degree, which is the ratio of the number of the granular voids in the end parts of the detection electrodes to the total number of the granular voids provided in the central part and the end parts of the detection electrodes, is within the range of 0.55 to 0.95.

* * * * *